United States Patent [19]

Larsson

[11] Patent Number: 4,794,915
[45] Date of Patent: Jan. 3, 1989

[54] METHOD FOR INDUCING UTERINE ACTIVITY THROUGH NIPPLE STIMULATION

[75] Inventor: Karl O. O. A. H. Larsson, Schweiz, Switzerland

[73] Assignee: ISG/AG, Zug, Switzerland

[21] Appl. No.: 9,330

[22] Filed: Jan. 30, 1987

Related U.S. Application Data

[63] Continuation-in-part of Ser. No. 811,002, Dec. 19, 1985, abandoned.

[30] Foreign Application Priority Data

Dec. 24, 1984 [CH] Switzerland ............... 6136/84

[51] Int. Cl.⁴ ............... A61H 23/04; A61H 7/00; A61M 1/06; A61M 1/00
[52] U.S. Cl. ............... 128/64; 604/74; 604/75; 128/44
[58] Field of Search ............... 128/44, 64, 67, 52, 128/31, 60, 61, 32, 38; 604/74, 75, 76; 119/14.52

[56] References Cited

U.S. PATENT DOCUMENTS

| | | | |
|---|---|---|---|
| 532,236 | 1/1895 | Hardesty | 128/38 |
| 956,325 | 4/1910 | Fey | 128/64 |
| 975,047 | 11/1910 | Klein et al. | 119/14.52 |
| 1,460,927 | 7/1923 | Thompson et al. | 128/67 |
| 2,000,710 | 5/1935 | Miller | 120/300 |
| 2,542,505 | 2/1951 | Gascoigne | 604/74 |
| 3,233,607 | 2/1966 | Bolie | 128/64 |
| 3,382,867 | 5/1966 | Reaves | 128/38 |
| 3,587,567 | 6/1971 | Schiff | 128/64 |
| 3,822,703 | 7/1974 | Davisson | 604/75 |
| 4,680,028 | 7/1987 | Stuart | 604/74 |

FOREIGN PATENT DOCUMENTS

| | | |
|---|---|---|
| 831799 | 7/1975 | Belgium . |
| 540934 | 12/1931 | Fed. Rep. of Germany . |
| 2451953 | 5/1976 | Fed. Rep. of Germany ... 119/14.52 |
| 2807646 | 8/1978 | Fed. Rep. of Germany ........ 604/75 |
| 599054 | 10/1925 | France . |
| 2995 | of 1911 | United Kingdom ........... 128/32 |
| 17778 | of 1915 | United Kingdom . |
| 168234 | 9/1921 | United Kingdom . |
| 660283 | 11/1951 | United Kingdom ........... 604/74 |

Primary Examiner—David Wiecking
Assistant Examiner—Tonya Lamb
Attorney, Agent, or Firm—Willian Brinks Olds Hofer Gilson & Lione Ltd.

[57] ABSTRACT

A method for mechanically stimulating the nipples of a pregnant woman for diagnostic and therapeutic effects. A nipple stimulator device is placed over a woman's nipple, and an intermittent reduced pressure is induced in the interior of the apparatus by a pump. An elastic membrane on the stimulator device is drawn inward by the reduced pressure, and in so doing acts to massage the breast nipple and the adjacent breast. A gentle, soft massage of the nipple is thereby provided to yield the desired stimulation to produce hormones, for example, useful in accelerating labor or conducting contraction stress tests in a pregnant woman.

17 Claims, 2 Drawing Sheets

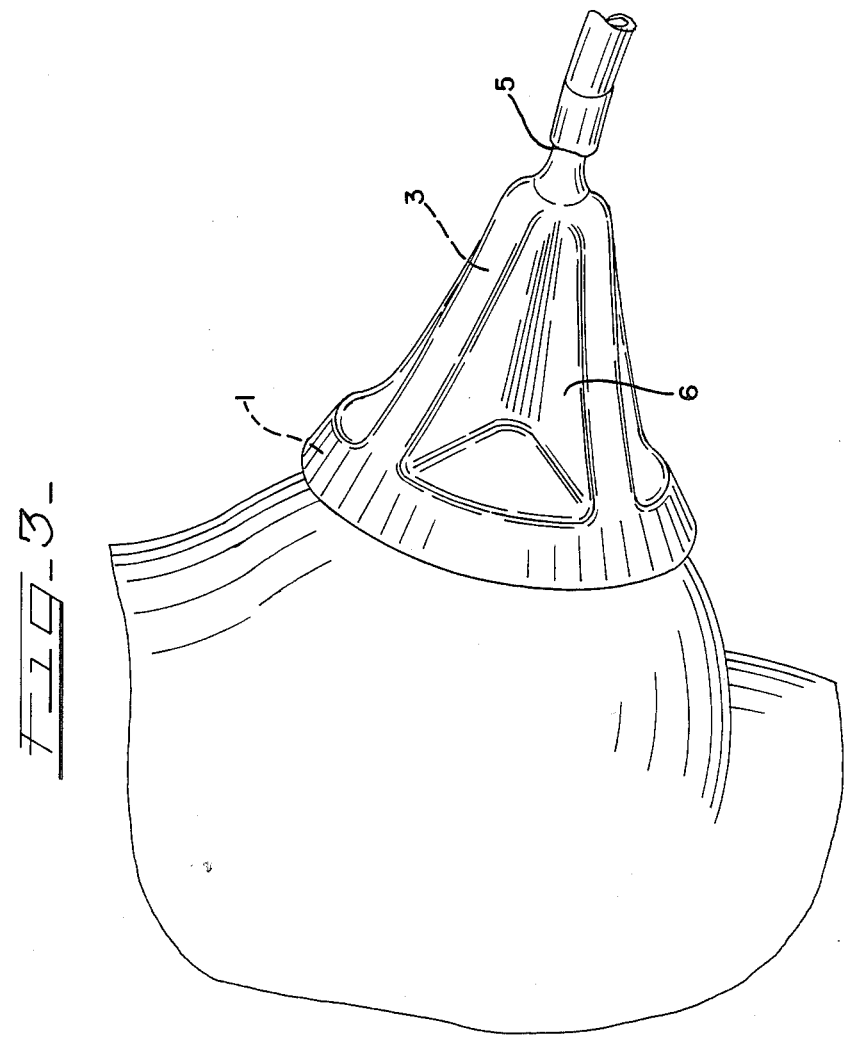
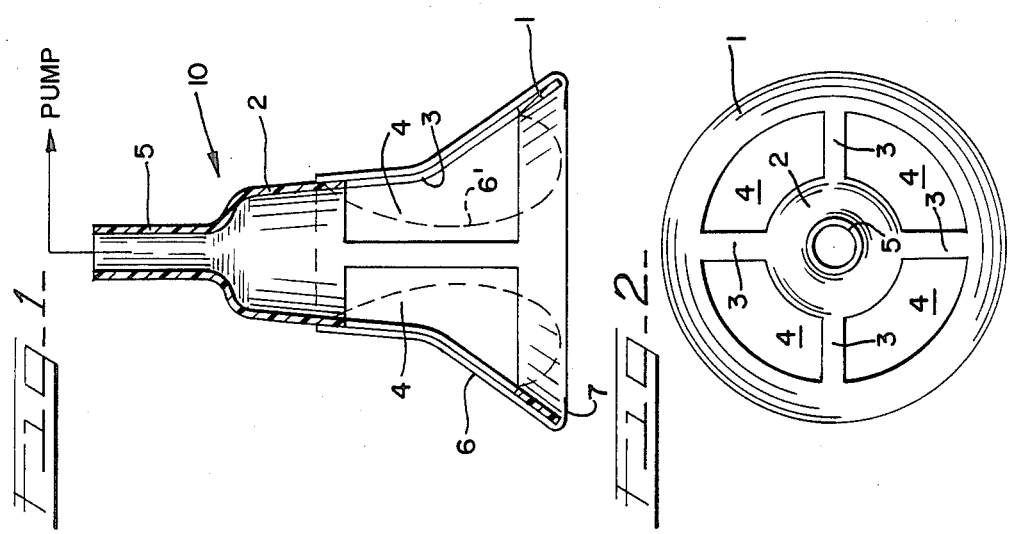

FIG_4a
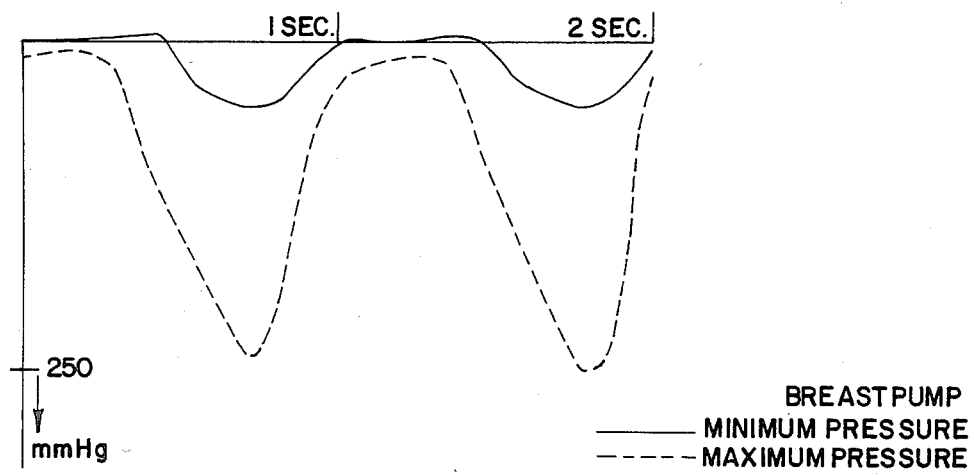
250
mmHg
BREAST PUMP
——— MINIMUM PRESSURE
----- MAXIMUM PRESSURE
FIG_4b
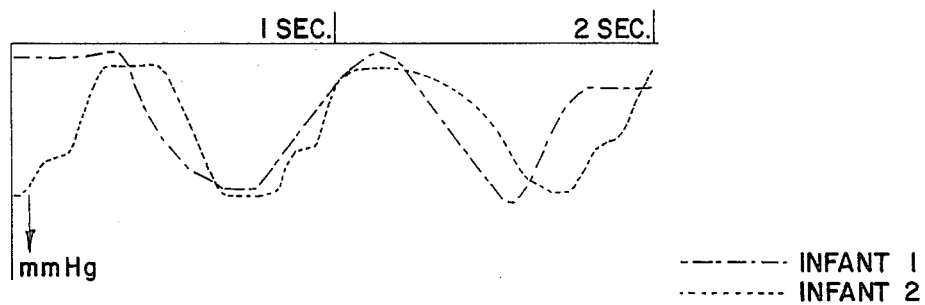
mmHg
—·—·— INFANT 1
·········· INFANT 2

METHOD FOR INDUCING UTERINE ACTIVITY THROUGH NIPPLE STIMULATION

The following patent application is a continuation-in-part of Ser. No. 06/811,002, filed Dec. 19, 1985, abandoned.

FIELD OF THE INVENTION

The invention relates to a method for the stimulation of the nipples of the breasts of a pregnant woman in order to, among other things, enhance the production of labor-inducing hormones, as well as enabling the performance of contraction stress tests.

BACKGROUND OF THE INVENTION

In practice, labor can often be difficult to induce in women. Quite frequently, uterine contractions will occur infrequently for long periods of time before increasing to the extent that the final stages of labor begin, and birth occurs. Yet inducing labor is a fairly simple task in theory.

Essentially, labor is stimulated naturally through the production of labor-inducing hormones (oxytocin) in a pregnant woman. Once these hormones attain a certain level in the woman's bloodstream, uterine contractions will increase to the rate that the final stages of birth will occur. Thus, where the natural output of these hormones is insufficient, the problem becomes one of stimulating the woman in order to create the production of this hormone, or providing a substitute for such stimulation.

Various ways of inducing uterine contractions have been attempted. For instance, oxytocin has been intravenously introduced into the body.

Research has shown that another method that increases the production of this hormone is to gently stimulate the nipples of the breasts of the pregnant woman. This stimulation gives the effect of a baby's suckling, which enhances the hormonal output to induce labor. Manual stimulation of the nipples is considered to be more desirable by many since it generates "natural" body hormones. It also avoids the intrusive delivery of Oxytocin, which is typically administered in an intravenous drip.

In recent years, nipple stimulation has been a common practice as a means for producing uterine contractions. This stimulation produces contractions in order to: (1) perform contraction stress tests, to judge the stress on the fetus; (2) to induce labor; (3) to ripen the cervix; and (4) to manage the period of labor just before birth.

Current methods of nipple stimulation have all been manual. They consist of the application of warm soaks, such as soaking the nipples with a warm damp cloth, the direct massage of nipples with gauze, indirect manual massage of the nipples through the clothes, and even use of a breastpump. Various tests have shown that hyperstimulation of the uterus often occurs with these manual methods, sometimes accompanied by fetal distress.

In addition, potential adverse effects occur during nipple stimulation through conventional methods. First, nipple discomfort may result from the application of too much pressure on the nipples. Second, there may be milk secretion during nipple stimulation, which may be distracting to both the pregnant woman as well as the individual applying the massage. Third, blisters may occur on overstimulating the nipples through excessive pressure, such as might be inadvertently applied by a breastpump. Fourth, there may be hyperstimulation of the uterus, which can result in fetal distress.

SUMMARY OF THE INVENTION

One object of the present invention is to produce uterine contractions mechanically through nipple stimulation in an improved manner for conducting contraction stress tests. These tests assess fetal heart rate changes as a measure of fetal well-being.

It is a further object of the invention to provide an improved method of nipple stimulation to alleviate certain complications of pregnancy through the augmentation or induction of labor.

These and other objects of the invention are accomplished through the method of nipple stimulation as the present invention which comprises the steps of first placing a special breast hood over the breast of a pregnant woman, and then operating the hood to massage the nipple. The special breast hood preferably comprises a bell shaped frame with large open areas and a membrane surrounding these open areas. The hood is then attached to an intermittent suction means, such as a pump. The pump causes the membrane to retract through the large open areas to contact and squeeze the nipple. When the suction is released, the membrane relaxes releasing the nipple. This stroking action massages and stimulates the nipple.

The method of the present system has found particular application using a modified electric breastpump. The pump is a breastpump with physiological nursing action, i.e., a suction cycle reminiscent of suckling, that has been used for expulsion of milk in nursing mothers.

The foregoing features and advantages of the invention will be further understood upon consideration of the following detailed description of an embodiment of the invention taken in conjunction with the drawings, in which:

BRIEF DESCRIPTION OF THE DRAWINGS

FIG. 1 is a sectional view along the axis of a breast hood made in accordance with the present invention;

FIG. 2 is a plan view looking upwardly and into the breast hood of FIG. 1;

FIG. 3 is a perspective view of the breast hood of FIG. 1 applied to a breast; and FIGS. 4a, 4b are graphic representations of the similarity in the action of suckling infants and the breastpump preferably used in the practice of the present invention.

DESCRIPTION OF AN EMBODIMENT OF THE INVENTION

The method of this invention has been practiced to advantage using a particular electric motor driven pneumatic breastpump and a specially developed breast shield or hood operated by the pump for nipple massage. While the invention is described hereafter with respect to these particular components, it will be understood that the method of this invention could be practiced with comparable equipment.

THE STIMULATION DEVICE

Basically, two aspects of a typical breastpump for the extraction of mother's milk, such as the Medela Mualectric breastpump, were modified for use in nipple stimulation according to the present invention, namely the vacuum control system and the breast shield.

The breastpump used is an electrically powered piston pump that has a physiological nursing action. Such a pump is the Manualectric breastpump supplied by Medela, P.O. Box 386, Crystal Lake, Ill. 60014. The main components of the pump are a cylinder/piston system, motor, and suction regulator valve. To produce the physiological nursing action, every pump cycle consists of three phases, with pressure measurements as follows.

In the suction phase, the normal pump setting will reduce pressure from atmospheric pressure of about 760 mm mercury to about 560–460 mm mercury, resulting in a negative pressure of about 200–300 mm mercury. In the suction phase, the minimum setting is a reduction in pressure of 90–120 mm mercury. In the release phase, negative pressure returns to atmospheric pressure of about 760 mm mercury. In the relaxation phase, there is a small positive pressure of about 10 mm mercury.

The pump operates at approximately 48 cycles per minute. This cycle with the foregoing phases produces a pressure rhythm that substantially follows the same pattern as a baby's regular rhythmic suckling cycles, each consisting of suction, release and relaxation.

As seen in FIGS. 4a and 4b, the motion of the pump approximates the natural suckling of an infant. In FIG. 4b, there are charted the suction pressure of two infants (approximately one week old). As seen in FIG. 4a, these cycles have been approximated in the mechanical breastpump used in the present invention.

A modification kit is used to convert the typical Medela Manualectric breastpump into the nipple stimulation device. The kit consists of an external pressure control gauge, a vacuum connection piece, an overflow safety bottle, and a specially designed breast hood. The external pressure control gauge, the special vacuum connection piece, and the overflow safety bottle are used to modify the vacuum control system of the pump. The specially designed breast hood, as shown in the Figures, massages the breast under action of the pump to produce nipple stimulation.

The specially designed breast hood consists of a hard medical grade polypropylene frame covered by a relatively thin membrane or sleeve of soft latex rubber. When the hood is applied to the breast around the nipples and a negative pressure developed within the hood, the rubber layer is drawn inwardly against the nipple; when the pump cycles, reducing the negative pressure, the rubber releases. Thus, the physiological nursing action of the pump causes the rubber to massage the nipple.

The apparatus shown in FIGS. 1–3 comprises a bell shaped carrier frame of plastic 10 having a base ring 1, a base part 2, and connecting crosspieces 3. Between the crosspieces 3 there are presented four large area roughly rectangular or trapezoidal shaped openings 4 in the upper end of the base 2. There is a connecting piece 5 for a suction line, as seen in FIG. 1. The suction line leads to the breastpump.

On the outside of the carrier frame 10, there is arranged a similar bell shaped sleeve or membrane 6 of rubber elastic material, for example translucent rubber or latex. The envelope 6 tightly seals off the openings 4 and surrounds the lower edge of the ring 1, forming a yielding cushion 7. The carrying frame 10 with the surrounding sleeve 6 yields a hood for emplacement on the woman's breast, as seen in FIG. 3.

The hood presents flexible wall parts as formed by the envelope 6 over the openings 4. By lightly pressing the apparatus over the breast, an airtight closure is formed, such that a negative pressure can be produced in the interior of the hood. As previously noted, negative pressure within the hood causes the elastic membrane 6 to be drawn through the openings 4 into the hood interior. Thus, the elastic membrane 6 deforms to approximate the form indicated in FIG. 1 as 6'. In the process, the nipple area and nipple tip are intermittently mechanically stroked and stimulated by the membrane material.

As seen in FIGS. 1 and 3, the openings 4 comprise the greatest area part of the bell-shaped carrier frame so that adjacent openings 4 lie separated from one another only by the crosspieces 3. The openings 4 should be of sufficient area to permit the membrane 6 to deform so that it surrounds and gently strokes the nipple.

APPLICATIONS AND PRACTICE OF THE METHOD

One application of the method of this invention is in the assessment of fetal well-being by contraction stress tests. These tests are often used in high-risk pregnancies, from 26 weeks gestation onwards, where placental insufficiency might be present or fetal compromise is being looked for. Examples of situations in which fetal assessment may be necessary include the following: intrauterine growth retardation, chronic hypertension, pregnancy induced hypertension, diabetes mellitus, postdates, and oligohydramnios. For all these situations, nipple stimulation can be used to produce intrauterine contractions to test the fetal heart rate.

Another application of the method of this invention is for the induction or augmentation of labor. Induction of labor may be necessary in various complications of pregnancies such as intrauterine growth retardation, postdates, hypertension, and diabetes mellitus.

Typically, all patients having vaginal delivery can be included for use of the present method. Certain prescribed steps will ordinarily be followed in practicing the method. First, petroleum jelly ointment is applied to a nipple of either breast. Before turning the pump on, the patient is placed on a fetal monitor. The fetal heart rate can thereby be observed. A tocodynanometer should also be used so that uterine activity is monitored.

Nipple stimulation is preferably begun after at least 10 minutes of stable fetal heart rate, and uterine activity of less than three contractions in a 10 minute period. After making sure the nipple is centered in the hood (FIG. 3), the patient holds the hood in place, preferably with the contralateral hand. Thus, the right hand holds the cup on the left breast and vice versa. If long stimulation is anticipated, two hoods may be applied, one on each breast, and kept in place by use of a disposable mesh brassiere, gauze or the like. The pump line is placed on the appropriate hood for stimulation.

The pump is then turned on to a minimum pressure of about 125 mm mercury. The soft rubber membrane 6 covering the hood framework 10 retracts around the nipple and releases each time negative pressure is applied and withdrawn in accordance with the physiological nursing cycle previously described. After three minutes of massage, if uterine activity is still inadequate and fetal heart rate has remained stable, the pressure may be increased to about 150 mm mercury.

After this point, the pressure may be increased every two minutes as needed to a maximum of about 250 to about 300 mm mercury, dependent upon whether contractions increase to the rate of at least three per 10 minutes.

Nipples should be alternated about every 5-10 minutes when performing a contraction stress test for determination of fetal stress, and about every 15-20 minutes when augmentation or induction of labor are performed. Before switching a hood to another breast, or changing the pump line from one hood to another where two hoods are used, the pressure should be reduced to a minimum to facilitate the changeover. The pressure may then be increased over the next minute to the same pressure used prior to the switch.

If contractions appear every two to three minutes, or more than three for every 10 minutes, the pressure should be decreased toward the minimum pressure of 125 mm mercury. Should contractions appear at two minute intervals or less, or if fetal heart rate changes are present, stimulation should be stopped. In most instances, uterine contractions will space out in a matter of several minutes and fetal heart rate changes will disappear.

It should be noted that pressure should be increased gradually since some patients are extremely sensitive to nipple stimulation and might hyperstimulate easily. If a patient complains of nipple discomfort, the pressure should be gradually reduced until the patient is comfortable. In addition, milk excretion during nipple stimulation may occur. For this reason a container can be provided with a connection to the pump line to prevent milk from being drawn into the pump during intermittent pressure changes.

The effects of the nipple stimulation method were observed in tests performed which serve as examples of the efficiency of the method of the present invention.

EXAMPLE I

In running this test, a contraction stress test was performed by nipple stimulation using the previously described electric breastpump. Contraction stress tests (CST) are frequently used in the pre-birth evaluation of fetal status. In this test 295 patients were surveyed and it was determined whether nipple stimulation of the present method produced at least three contractions per 10 minutes. The following chart demonstrates the success rate of the CST:

| CST result | No. of tests | % | Time interval stimulation to contractions (min.) | Total time of stimulation (min.) |
| --- | --- | --- | --- | --- |
| Successful | 248 | 84.04 | 6.61 ±4.94 | 18.35 ±9.18 |
| Failed | 47 | 15.96 | — | 30.23 ±8.36 |

Much less hyperstimulation (about 4.4%) was encountered with the device when compared to studies done with manual stimulation, which resulted in hyperstimulation of rates of up to 55%. Side effects were minimal and patient acceptance was excellent. Patients perceived the pump as a scientific and more accurate way of achieving nipple stimulation as well as a more aesthetic one. The manual methods used instead of the mechanical nipple stimulation method, i.e., massaging of the nipple and applying warmth or softly stroking the areola, are perceived by patients as unaesthetic or embarrassing, and therefore, unacceptable. An additional problem is that the use of manual method causes a lack in uniformity in stimulation, which is not present in the method of this invention.

EXAMPLE II

In this test, 30 women undergoing labor were tested using the present invention against 32 receiving oxytocin in the traditional injection form. Measurements were made for the time interval to achieve regular contractions and the success rate of movement into the active phase of labor. Results were as follows:

| | Labor Induction Time Intervals | | |
| --- | --- | --- | --- |
| | Time from Stimulation to 3 uterine contractions per 10 min (min) | Time from Stimulation to active phase (hr) | Failed* |
| Breastpump (30) | 5.68 ± 6.13 | 4.84 ± 3.33 | 3 |
| Oxytocin (32) | 61.55 ± 42.62 | 6.90 ± 4.21 | 4 |

*Failed induction = failure to reach the active phase of labor

Thus, on the average, uterine contractions occurred quicker, as did the time to reach the active phase of labor.

EXAMPLE III

A study was made of movement into the third stage of labor (the "active" stage of labor) for 85 patients, 32 of whom used the method of nipple stimulation of this invention and 53 of whom had oxytocin injections. The hematocrit levels and blood loss for both groups as well as the duration of the third stage of labor were approximately the same. Nipple stimulation for induced uterine contractions provided a safe and reasonable alternative to the traditional management of the third stage of labor with Oxytocin.

It will be understood from the preceding description that various changes made in the indicated method by those familiar with this art are possible yet still fall within the scope of the invention.

What is claimed is:

1. A method of nipple stimulation for the production of intrauterine contractions, comprising the steps of:
    placing a breast hood over the breast of a pregnant woman, said hood comprising a frame with large passages and a membrane around said large passages;
    attaching said hood to an intermittent suction means, said intermittent suction means causing said membrane to retract through said large passages around the nipple, and
    operating said intermittent suction means to gently massage and stimulate the nipple in a manner to elicit normal contraction-inducing hormones without significant expression of milk.

2. A method of nipple stimulation for the production of intrauterine contractions, comprising the steps of:
    placing a nipple stimulator hood over the breast of a pregnant woman with said hood surrounding the nipple, said nipple stimulator hood comprised of a frame having a base and large area passages on an outer surface, a soft rubber membrane attached to said frame over said base and said outer surface, and means for connecting the interior space of said hood to an intermittently operating suction pump;

creating an airtight seal by causing the soft rubber membrane covering said base to press against the breast;

attaching said connecting means on the nipple stimulator hood to said intermittent suction pump; and operating said suction pump such that said soft rubber membrane retracts around the nipple and then releases whenever negative pressure is applied and withdrawn, said intermittent pressure causing stimulation of the nipple by gentle massage, thereby eliciting normal contraction-inducing hormones without significant expression of milk by said massage.

3. The method of claim 2 wherein nipple stimulation occurs at a rate of about 48 strokes per minute.

4. The method of claim 3 wherein said soft rubber membrane is comprised of latex.

5. The method of claim 3 wherein said intermittent pump pressure begins at about 125 mm mercury and is increased to a maximum in the range of about 250–300 mm Hg for inducing the production of labor enhancing hormones in a pregnant woman.

6. The method of claim 3 wherein nipple stimulation is alternated between breasts by means of disconnecting said pump from said hood and attaching said pump to a second hood covering the opposite breast, then operating said pump said that said soft rubber membrane retracts around the nipple of the second breast and then releases whenever negative pressure is applied and withdrawn, said intermittent pressure causing stimulation of said nipple of said second breast.

7. The method of claim 5 wherein nipple stimulation is alternated between breasts about every 15–20 minutes when augmentation or induction of labor is performed.

8. The method of claim 5 wherein nipple stimulation is alternated between breasts about every 5–10 minutes when performing a contraction stress test.

9. The method of claim 8 wherein said method causes contractions in pregnant women at the rate of about 3 contractions for about every 10 minutes.

10. A method for stimulating the nipples of a pregnant woman for the production of intrauterine contractions comprising the steps of:

providing hood means for surrounding the nipple and adjacent breast and for massaging the nipple, said hood means including a flexible sleeve within which the nipple and breast are received, which sleeve is generally airtight and can be evacuated when said hood means is applied to the breast in generally sealing engagement therewith, and means for carrying said flexible sleeve, attaching said hood means to a suction means for evacuating said flexible sleeve, intermittently and rythmically evacuating said flexible sleeve with said suction means to contract said flexible sleeve about the nipple to gently massage and stimulate the nipple, thereby eliciting normal contraction-inducing hormones without significant expression of milk by said massage.

11. The method of claim 10 wherein said means for carrying said flexible sleeve is a bell-shaped rigid frame having large open areas formed therethrough, said flexible sleeve surrounding said frame and overlying said open areas, said suction means causing said sleeve to contract through said open areas to massage and stimulate the nipple.

12. The method of claim 11 wherein said nipple stimulation occurs at a rate of about 48 strokes per minute.

13. The method of claim 12 wherein said flexible sleeve is comprised of latex.

14. The method of claim 12 wherein said intermittent pump pressure begins at about 125 mm mercury and is increased to a maximum in the range of about 250–300 mm Hg for inducing the production of labor enhancing hormones in a pregnant woman.

15. The method of claim 14 wherein said nipple stimulation is alternated between breasts about every 15–20 minutes when augmentation or induction of labor is performed.

16. The method of claim 14 wherein said nipple stimulation is alternated between breasts about every 5–10 minutes when performing a contraction stress test.

17. The method of claim 16 wherein said method causes contractions in pregnant women at the rate of 3 for about every 10 minutes.

* * * * *

UNITED STATES PATENT AND TRADEMARK OFFICE
CERTIFICATE OF CORRECTION

PATENT NO. : 4,794,915
DATED : January 3, 1989
INVENTOR(S) : Karl O.A.H. Larsson It is certified that error appears in the above-identified patent and that said Letters Patent is hereby corrected as shown below:

In column 2, line 67, please delete "Mualectric" and substitute therefor --Manualectric--.

IN THE CLAIMS

In column 7, line 28, please delete "said" and substitute therefor --such--.

Signed and Sealed this

Eighth Day of October, 1991

Attest:

HARRY F. MANBECK, JR.

Attesting Officer    Commissioner of Patents and Trademarks